United States Patent
Hung et al.

(10) Patent No.: US 8,434,366 B2
(45) Date of Patent: May 7, 2013

(54) ACTIVE DETECTION TECHNIQUES FOR PHOTOACOUSTIC SENSORS

(75) Inventors: Chih-Ming Hung, McKinney, TX (US); Django Trombley, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 338 days.

(21) Appl. No.: 12/969,160

(22) Filed: Dec. 15, 2010

(65) Prior Publication Data

US 2012/0151994 A1 Jun. 21, 2012

(51) Int. Cl.
*G01N 29/04* (2006.01)
*G01N 21/17* (2006.01)

(52) U.S. Cl.
USPC .............. 73/643; 73/24.02; 73/649

(58) Field of Classification Search ............ 73/643, 73/579, 645, 648, 649, 24.01, 24.02, 24.06
See application file for complete search history.

(56) References Cited

U.S. PATENT DOCUMENTS

| | | | | |
|---|---|---|---|---|
| 4,051,371 A * | 9/1977 | Dewey et al. | ............ | 250/339.09 |
| 4,055,764 A * | 10/1977 | Dimeff | ............ | 250/336.1 |
| 4,184,768 A | 1/1980 | Murphy et al. | | |
| 4,818,882 A | 4/1989 | Nexo et al. | | |
| 5,375,595 A * | 12/1994 | Sinha et al. | ............ | 600/402 |
| 5,479,259 A | 12/1995 | Nakata et al. | | |
| 6,106,245 A | 8/2000 | Cabuz | | |
| 6,608,683 B1 * | 8/2003 | Pilgrim et al. | ............ | 356/432 |
| 7,245,380 B2 | 7/2007 | Kosterev | | |
| 7,387,021 B2 | 6/2008 | DiFoggio | | |
| 7,520,158 B2 | 4/2009 | DiFoggio | | |
| 7,605,922 B2 | 10/2009 | Willing et al. | | |
| 7,797,983 B2 | 9/2010 | Kauppinen | | |
| 8,096,165 B2 * | 1/2012 | Crane | ............ | 73/24.02 |
| 8,175,822 B2 * | 5/2012 | Baron et al. | ............ | 702/54 |
| 8,312,758 B2 * | 11/2012 | Tobias | ............ | 73/24.02 |
| 2008/0252891 A1 | 10/2008 | Uber | | |
| 2009/0320561 A1 | 12/2009 | Fritz et al. | | |
| 2010/0027012 A1 | 2/2010 | Fritz et al. | | |

FOREIGN PATENT DOCUMENTS

EP  0 685 728  12/1995

* cited by examiner

*Primary Examiner* — J M Saint Surin
(74) *Attorney, Agent, or Firm* — Alan R. Cooper; Wade J. Brady, III; Frederick J. Telecky, Jr.

(57) ABSTRACT

Traditional photoacoustic sensors generally operate in a passive mode, which can degrade the performance. Here, however, a photoacoustic sensor has been disclosed that operates an acoustic resonance chamber and a transducer in an active mode so as to avoid the problems associated with traditional photoacoustic sensors; in particular, because the acoustic resonance chamber operates at near atmospheric pressure such as 100's Torr as opposed to 1 m Torr type of pressure for radio spectroscopy, the sensor is allowed to be scaled to operate on an integrated circuit or IC.

35 Claims, 3 Drawing Sheets

ACTIVE DETECTION TECHNIQUES FOR PHOTOACOUSTIC SENSORS

TECHNICAL FIELD

The invention relates generally to photoacoustic sensors and, more particularly, to active detection techniques for photoacoustic sensors.

BACKGROUND

Photoacoustic sensors have been employed in the past for detection of gas species. Turning to FIG. 1, an example of a conventional photoacoustic sensor system 100 can be seen. This system 100 generally comprises a laser 102, optics 104, and an acoustic resonance chamber 106, tuning fork 108, lock-in amplifier 110, and function generator 112. In operation, the function generator 112 provides a drive signal to the laser 102 so as to modulate the beam emitted by the laser 102. The optics 104 can focus the beam along optical path 114 into the acoustic resonance chamber 106 (which contains a gas sample). By virtue of the photoacoustic effect, the modulated laser beam will cause the gas sample in the acoustic resonance chamber 106 to expand and relax if the wavelength of the laser matches the molecular resonance of the gas sample, which, in turn, causes the acoustic resonance chamber 106 to vibrate. Tuning fork 108 (which is generally placed in proximity to the acoustic resonance chamber 106 and which is generally a high-Q resonator) converts the vibrational signatures to electrical signals which is then amplified by the lock-in amplifier 110 (which also can receive the drive signal from the function generator 112). Based on the vibrational signatures, the identities and concentrations of gas species within the gas sample can be isolated.

This arrangement, however, does have some problems. For example, because this system 100, uses passive detection, the system 100 suffers from errors due to amplifier noise (i.e., used to amplify the signal from tuning fork 108) and ambient thermal noise as well as frequency drift and inaccuracy of tuning fork natural resonance. Therefore, there is a need for an improved photoacoustic sensor.

Some other conventional systems are: U.S. Pat. No. 4,184,768 U.S. Pat. No. 4,818,882; U.S. Pat. No. 5,479,259; U.S. Pat. No. 6,106,245; U.S. Pat. No. 7,245,380; U.S. Pat. No. 7,387,021; U.S. Pat. No. 7,520,158; U.S. Pat. No. 7,605,922; U.S. Pat. No. 7,797,983; U.S. Patent Pre-Grant Publ. No. 2008/0252891; U.S. Patent Pre-Grant Publ. No. 2009/0320561; U.S. Patent Pre-Grant Publ. No. 2010/0027012; and European Patent No. EP0685728.

SUMMARY

A preferred embodiment of the present invention, accordingly, an apparatus is provided. The apparatus comprises a transmitter that generates a modulated energy beam along an axis; an acoustic resonance chamber that is generally coextensive with the axis and that receives the modulated energy beam; an acoustic transducer that is placed in proximity to the acoustic resonance chamber; drive circuitry that is electrically coupled to the transmitter, wherein the drive circuitry is adapted to operate the acoustic resonance chamber based on the resonant frequency of the acoustic transducer operating in an active resonance mode; and a detector that is electrically coupled to the acoustic transducer and the drive circuitry, wherein the detector detects the existence of resonance of the acoustic resonance chamber by detecting a change in the frequency or amplitude of an oscillator formed by the drive circuitry and the acoustic transducer.

In accordance with a preferred embodiment of the present invention, the detector further comprises a frequency counter.

In accordance with a preferred embodiment of the present invention, the detector further comprises a phase detector.

In accordance with a preferred embodiment of the present invention, the detector further comprises a phase-locked loop (PLL).

In accordance with a preferred embodiment of the present invention, the detector further comprises an analog-to-digital converter (ADC).

In accordance with a preferred embodiment of the present invention, the transmitter further comprises: an emitter that emits the modulated energy beam, wherein the oscillator gates the emitter at a gating frequency; and a focusing member that is generally coextensive with the axis so as to focus the modulated energy beam.

In accordance with a preferred embodiment of the present invention, the emitter further comprises a laser diode, and wherein the modulated energy beam further comprises a modulated laser beam.

In accordance with a preferred embodiment of the present invention, the emitter further comprises an antenna that is adapted to emit RF radiation that generally matches a predetermined molecular resonant frequency, and wherein the focusing member further comprises a waveguide.

In accordance with a preferred embodiment of the present invention, the detector is electrically coupled to the drive circuitry to control the gating frequency so that the gating frequency generally matches the resonant frequency of the acoustic resonance chamber.

In accordance with a preferred embodiment of the present invention, the transmitter further comprises: a frequency generator that generates frequencies at resonant frequencies of molecules of a gas sample; the oscillator having the acoustic transducer and the drive circuitry as a negative resistance; an emitter that is electrically coupled to the frequency generator and that emits the modulated energy beam, wherein the oscillator modulates the frequency generator at a modulating frequency; and a focusing member that is generally coextensive with the axis so as to focus the modulated energy beam.

In accordance with a preferred embodiment of the present invention, the detector is electrically coupled to the drive circuitry to control an oscillating frequency formed by the transducer and the drive circuitry so that the modulating frequency generally matches the resonant frequency of the acoustic resonance chamber.

In accordance with a preferred embodiment of the present invention, the detector is electrically coupled to the drive circuitry to control the resonance chamber so that the chamber resonance generally matches the frequency of oscillation formed by the acoustic transducer and the drive circuitry.

In accordance with a preferred embodiment of the present invention, the drive circuitry further comprises: a current source that is electrically coupled to the acoustic transducer; and an NPN transistor that is electrically coupled to the current source at its collector and the acoustic transducer at its base.

In accordance with a preferred embodiment of the present invention, the drive circuitry further comprises: an inverting gain element that is electrically coupled between a first node and a second node; a first resistor that is electrically coupled between the first node and the second node; the acoustic transducer is electrically coupled between the first node and the second node; a first capacitor that is coupled to the first node; and a second capacitor that is coupled to the second node.

In accordance with a preferred embodiment of the present invention, the first and second capacitors further comprise first and second variable capacitors.

In accordance with a preferred embodiment of the present invention, the acoustic resonance chamber further comprises a tuning member that is adapted to adjust the resonant frequency of the acoustic resonant chamber.

In accordance with a preferred embodiment of the present invention, an integrate circuit (IC) is provided. The IC comprises a substrate; a transmitter that is formed on the substrate and that is adapted to generate a modulated energy beam along an axis; an acoustic resonance chamber that is formed on the substrate, that is generally coextensive with the axis and that is adapted to receive the modulated energy beam; a transfer system that is formed on the substrate and that is in fluid communication with the acoustic resonance chamber, wherein the transfer system is adapted to transfer fluid samples into the acoustic resonance chamber; an acoustic transducer that is formed on the substrate and that is placed in proximity to the acoustic resonance chamber; drive circuitry that is formed on the substrate and that is electrically coupled to the transmitter, wherein the drive circuitry is adapted to operate the acoustic resonance chamber based on the resonant frequency of the acoustic transducer operating in an active resonance mode; and a detector that is formed on the substrate and that is electrically coupled to the acoustic transducer and the drive circuitry, wherein the detector detects the existence of resonance of the acoustic resonance chamber by detecting a change in the frequency or amplitude of an oscillator formed by the drive circuitry and the acoustic transducer.

In accordance with a preferred embodiment of the present invention, the acoustic transducer further comprises a microelectromechanical systems (MEMS) microphone.

In accordance with a preferred embodiment of the present invention, transfer system further comprises: an input port that is in fluid communication with the acoustic resonance chamber; a first MEMS valve that is located between the input port and the acoustic resonance chamber; a output port that is in fluid communication with the acoustic resonance chamber; a second MEMS valve that is located between the output port and the acoustic resonance chamber; and a MEMS pump that is in fluid communication with the output port.

In accordance with a preferred embodiment of the present invention, the acoustic resonance chamber further comprises a tuning member that is adapted to adjust the resonant frequency of the acoustic resonant chamber.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
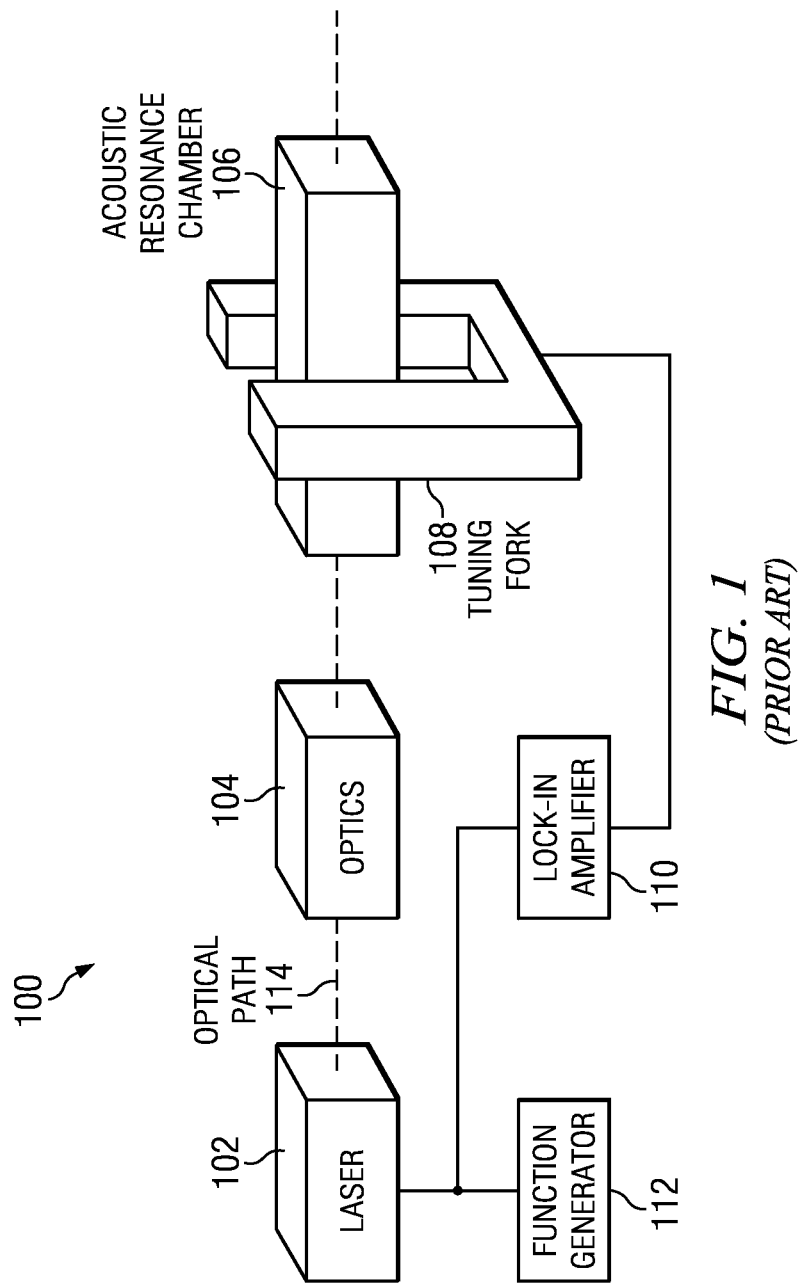
FIG. 1 is a block diagram of a conventional photoacoustic sensor system.

Refer now to the drawings wherein depicted elements are, for the sake of clarity, not necessarily shown to scale and wherein like or similar elements are designated by the same reference numeral through the several views.

Figure 2:
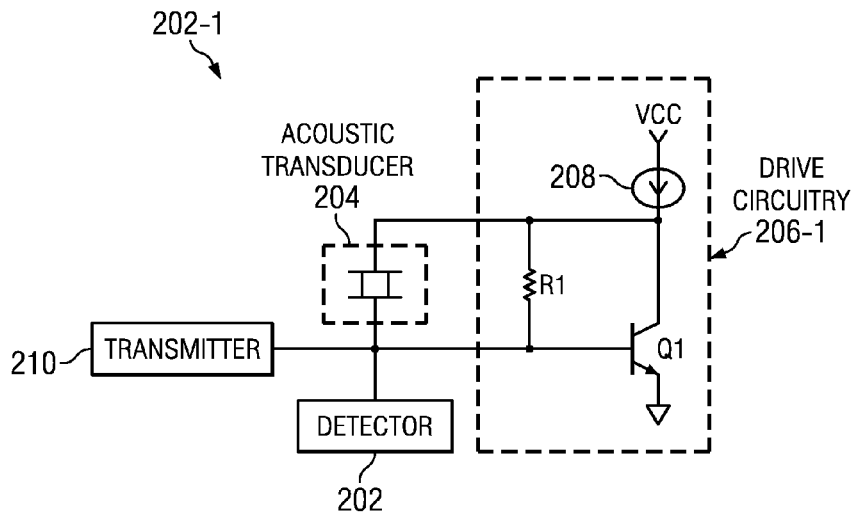
FIGS. 2 and 3 are block diagrams of examples of portions of a photoacoustic sensor system in accordance with a preferred embodiment of the present invention.

Turning to FIG. 2, an example of a portion 200-1 of a photoacoustic sensor can be seen. As shown, portion 200 generally uses an active resonance circuit or drive circuitry 206-1 to operate acoustic transducer 204 (i.e., piezoelectric crystal or microelectromechanical (MEMS) microphone) in an active resonance mode. In addition to the drive circuit 206-1, the portion also generally comprises a detector 202 and transmitter 210. The transmitter 210 can include both an emitter (i.e., diode laser or RF transmitter) and a frequency generator. Additionally, the drive circuit 206-1 generally comprises a current source 208 and a transistor Q1 (which can, for example, be an NPN transistor), while the resonator (not shown) can generally include an acoustic transducer 204 that is placed in proximity (i.e., 0.1 µm to 10 mm) to an acoustic resonance chamber (i.e., 106) such that the acoustic transducer 204 is able to vibrate or oscillate.

In operation, the drive circuitry 206-1 actively drives the acoustic transducer 204 so as to control the modulation of the beam used to drive the resonant chamber. Generally, a current is provided from current source 208 (from voltage rail VCC), while resistor R1 and transistor Q1 drive the acoustic transducer 204. Because the voltage-to-phase noise up conversion is generally filtered by the resonator (which is generally a high-Q resonator), the timing jitter is low and the frequency shift can be reliably detected. The detector 202 (which, for example, can be a phase detector or phase locked loop (PLL)) such that the detector 202 detects the existence of resonance of the acoustic resonance chamber by detecting a change in the frequency of the Pierce oscillator formed by the drive circuitry 202 (which can offer negative resistance) and the acoustic transducer 204. Typically, a reference resonator circuit or PLL can be used to establish a reference frequency to perform phase detection, where the first derivative of phase difference can be used to detect the frequency change. This frequency change can then be used to determine gas species present in a gas sample. Moreover, because system 200-1 generally operates the transducer in an active resonance mode, the oscillation and the modulation frequency track each other such that the detection of acoustic chamber resonance can be at the maximum sensitivity point of the transducer. Alternatively, the detector 202 may include a frequency counter.

Figure 3:
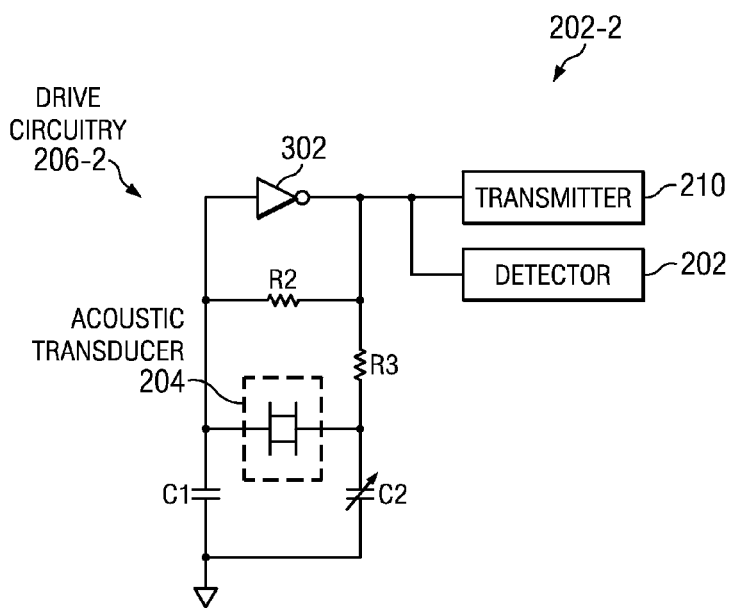

Turning to FIG. 3, another example of a drive circuitry 206-2 can be seen (which is used within portion 200-2 and which is also a Pierce oscillator). As shown, this drive circuitry 206-2 generally comprises an inverter 302, resistors R2 and R3, capacitor C1 and variable capacitor C2 (which, for example, can be one or more varactors or a switched capacitor bank). Alternatively, capacitor C1 can also be a variable capacitor. A difference between drive circuitry 206-1 and 206-2 is that the drive circuitry 206-2 can "tune" the oscillator 204 by adjusting or varying the capacitance of capacitor C2. As an alternative, a Colpitts oscillator can be used as well.

Figure 4:
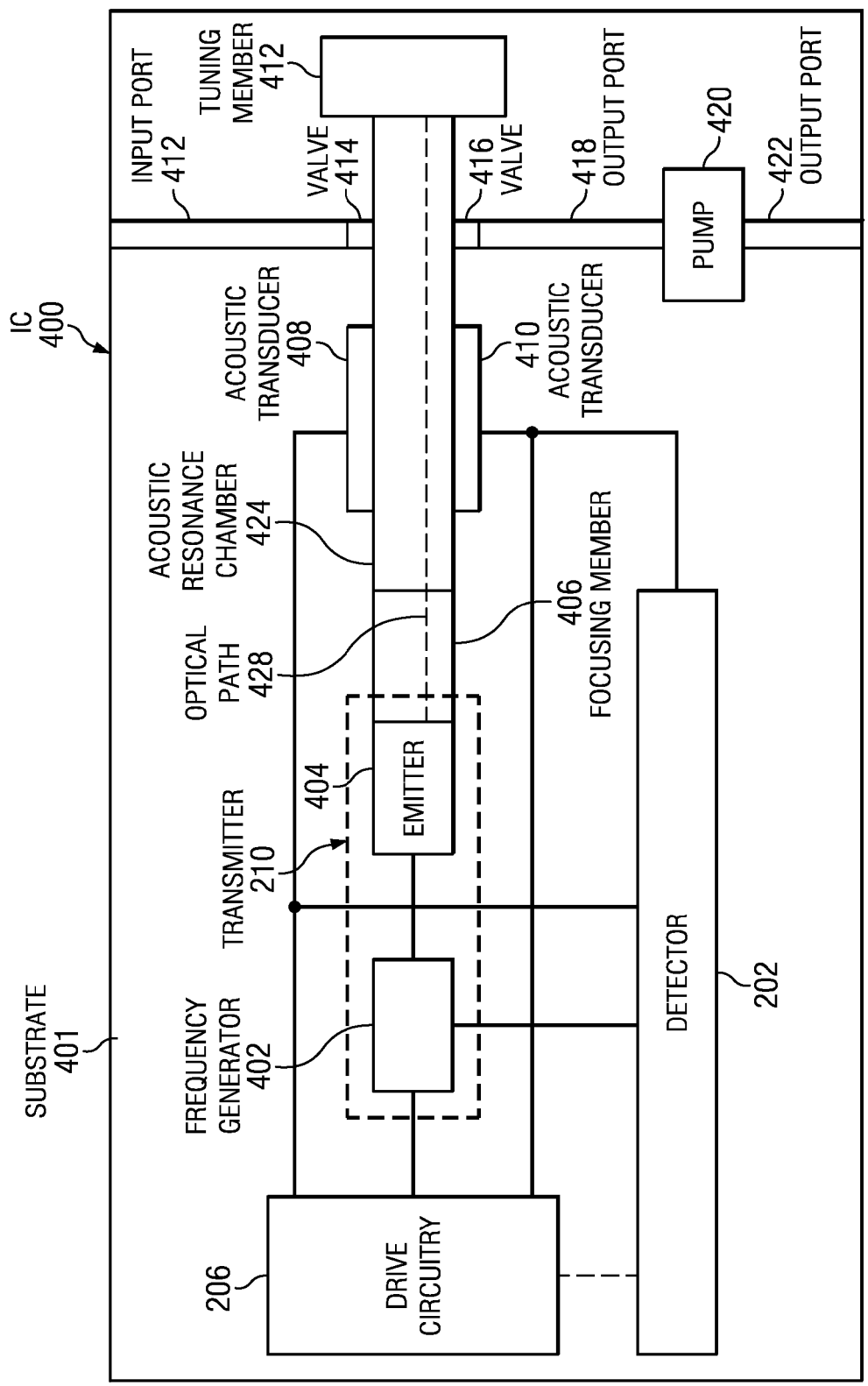
FIG. 4 is a block diagram of an example of a photoacoustic sensor system using the portions of FIG. 2 or FIG. 3.

In FIG. 4, an example of an IC 400 that employs a photoacoustic sensor system formed on a substrate 401 in accordance with a preferred embodiment of the present invention can be seen. IC 400 generally comprises drive circuitry 206-1 or 206-2 (hereinafter referred to as drive circuitry 206), detector 202, transmitter 210 (which, as shown and for example, can be a frequency generator 402 and emitter 404), focusing member 406 (which, for example, can be optics or a waveguide), acoustic transducers 408 and 410 (which, for example and as shown, can be a quartz crystal or MEMS microphones), acoustic resonance chamber 424, tuning member 426, input port 412, output ports 418 and 422, pump 420 (which, for example and as shown, can be a MEMS pump, such as those described in U.S. Pat. No. 6,106,245, which is incorporated by reference), and valves 414 and 416 (which, for example and as shown, can be MEMS valves). In operation, the transfer system or, collectively, valves 414 and 416 and pump 420 (which are in fluid communication with each other and the external atmosphere) can be used to introduce a gas sample to acoustic resonance chamber 424 and adjust the pressure within the acoustic resonance chamber to a desired pressure (i.e., 750 Torr). With the gas sample in place in this example, the frequency generator 402 generates an RF signal at resonant frequencies of molecules of the gas sample. The RF signal is then modulated by the drive circuitry 206 in either frequency generator 402 or emitter 404 so that a modulated beam (i.e., infrared laser, ultraviolet laser, visible light laser, or RF radiation) is emitted by the emitter 404 at a gating frequency, which is further focused along optical axis or path 428 by focusing member 406, so as to interact with the gas sample. The transducers 408 and 410 (i.e., quartz crystal or MEMS microphones) are placed in proximity to the acoustic resonance chamber 424 so that the detector 202 can detect the existence of resonance of the acoustic resonance chamber by detecting a change in the frequency of the oscillator formed by the drive circuitry 206 and the acoustic transducers 406 and 408. Additionally, the drive circuitry 206 and/or detector 202 can also provide a signal to control the tuning member 426 so as to vary the natural frequency of the acoustic resonance chamber 424 by, for example, extending or reducing the length of a generally cylindrical acoustic resonance chamber 242.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Accordingly, it is appropriate that the appended claims be construed broadly and in a manner consistent with the scope of the invention.

The invention claimed is:

1. An apparatus comprising:
    a transmitter that generates a modulated energy beam along an axis;
    an acoustic resonance chamber that is generally coextensive with the axis and that receives the modulated energy beam;
    an acoustic transducer that is placed in proximity to the acoustic resonance chamber;
    drive circuitry that is electrically coupled to the transmitter, wherein the drive circuitry is configured to operate the acoustic resonance chamber based on the resonant frequency of the acoustic transducer operating in an active resonance mode; and
    a detector that is electrically coupled to the acoustic transducer and the drive circuitry, wherein the detector detects the existence of resonance of the acoustic resonance chamber by detecting a change in the frequency or amplitude of an oscillator formed by the drive circuitry and the acoustic transducer.

2. The apparatus of claim 1, wherein the detector further comprises a frequency counter.

3. The apparatus of claim 1, wherein the detector further comprises a phase detector.

4. The apparatus of claim 1, wherein the detector further comprises a phase-locked loop (PLL).

5. The apparatus of claim 1, wherein the detector further comprises an analog-to-digital converter (ADC).

6. The apparatus of claim 1, wherein the transmitter further comprises:
    an emitter that emits the modulated energy beam, wherein the oscillator gates the emitter at a gating frequency; and
    a focusing member that is generally coextensive with the axis so as to focus the modulated energy beam.

7. The apparatus of claim 6, wherein the emitter further comprises a laser diode, and wherein the modulated energy beam further comprises a modulated laser beam.

8. The apparatus of claim 6, wherein the emitter further comprises an antenna that is adapted to emit RF radiation that generally matches a predetermined molecular resonant frequency, and wherein the focusing member further comprises a waveguide.

9. The apparatus of claim 6, wherein the detector is electrically coupled to the drive circuitry to control the gating frequency so that the gating frequency generally matches the resonant frequency of the acoustic resonance chamber.

10. The apparatus of claim 1, wherein the transmitter further comprises:
    a frequency generator that generates frequencies at resonant frequencies of molecules of a gas sample;
    the oscillator having the acoustic transducer and the drive circuitry as a negative resistance;
    an emitter that is electrically coupled to the frequency generator and that emits the modulated energy beam, wherein the oscillator modules the frequency generator at a modulating frequency; and
    a focusing member that is generally coextensive with the axis so as to focus the modulated energy beam.

11. The apparatus of claim 1, wherein the detector is electrically coupled to the drive circuitry to control an oscillating frequency formed by the transducer and the drive circuitry so that the modulating frequency generally matches the resonant frequency of the acoustic resonance chamber.

12. The apparatus of claim 1, wherein the detector is electrically coupled to the drive circuitry to control the resonance chamber so that the chamber resonance generally matches the resonant frequency of the acoustic transducer.

13. The apparatus of claim 1, wherein the drive circuitry further comprises:
    a current source that is electrically coupled to the acoustic transducer; and
    an NPN transistor that is electrically coupled to the current source at its collector and the acoustic transducer at its base.

14. The apparatus of claim 1, wherein the drive circuitry further comprises:
    an inverting gain element that is electrically coupled between a first node and a second node;
    a first resistor that is electrically coupled between the first node and the second node;

the acoustic transducer is electrically coupled between the first node and the second node;
a first capacitor that is coupled to the first node; and
a second capacitor that is coupled to the second node.

15. The apparatus of claim 13, wherein the first and second capacitors further comprise first and second variable capacitors.

16. The apparatus of claim 1, wherein the acoustic resonance chamber further comprises a tuning member that is adapted to adjust the resonant frequency of the acoustic resonant chamber.

17. An integrated circuit (IC) comprising:
a substrate;
a transmitter that is formed on the substrate and that is configured to generate a modulated energy beam along an axis;
an acoustic resonance chamber that is formed on the substrate, that is generally coextensive with the axis and that is configured to receive the modulated energy beam;
a transfer system that is formed on the substrate and that is in fluid communication with the acoustic resonance chamber, wherein the transfer system is configured to transfer fluid samples into the acoustic resonance chamber;
an acoustic transducer that is formed on the substrate and that is placed in proximity to the acoustic resonance chamber;
drive circuitry that is formed on the substrate and that is electrically coupled to the transmitter, wherein the drive circuitry is configured to operate the acoustic resonance chamber based on the resonant frequency of the acoustic transducer operating in an active resonance mode; and
a detector that is formed on the substrate and that is electrically coupled to the acoustic transducer and the drive circuitry, wherein the detector detects the existence of resonance of the acoustic resonance chamber by detecting a change in the frequency or amplitude of an oscillator formed by the drive circuitry and the acoustic transducer.

18. The IC of claim 17, wherein the detector further comprises a frequency counter.

19. The IC of claim 17, wherein the detector further comprises a phase detector.

20. The IC of claim 17, wherein the detector further comprises a PLL.

21. The IC of claim 17, wherein the detector further comprises an ADC.

22. The IC of claim 17, wherein the transmitter further comprises:
an emitter that emits the modulated energy beam, wherein the oscillator gates the emitter at a gating frequency; and
a focusing member that is generally coextensive with the axis so as to focus the modulated energy beam.

23. The IC of claim 22, wherein the emitter further comprises a laser diode, and wherein the modulated energy beam further comprises a modulated laser beam.

24. The IC of claim 22, wherein the emitter further comprises an antenna that is adapted to emit RF radiation that generally matches a predetermined molecular resonant frequency, and wherein the focusing member further comprises a waveguide.

25. The IC of claim 22, wherein the detector is electrically coupled to the drive circuitry to control the gating frequency so that the gating frequency generally matches the resonant frequency of the acoustic resonance chamber.

26. The IC of claim 17, wherein the transmitter further comprises:
a frequency generator that generates frequencies at resonant frequencies of molecules of a gas sample;
the oscillator having the acoustic transducer and the drive circuitry as a negative resistance;
an emitter that is electrically coupled to the frequency generator and that emits the modulated energy beam, wherein the oscillator modules the frequency generator at a modulating frequency; and
a focusing member that is generally coextensive with the axis so as to focus the modulated energy beam.

27. The IC of claim 17, wherein the detector is electrically coupled to the drive circuitry to control an oscillating frequency formed by the transducer and the drive circuitry so that the modulating frequency generally matches the resonant frequency of the acoustic resonance chamber.

28. The IC of claim 17, wherein the detector is electrically coupled to the drive circuitry to control the resonance chamber so that the chamber resonance generally matches the resonant frequency of the acoustic transducer.

29. The IC of claim 17, wherein the drive circuitry further comprises:
a current source that is electrically coupled to the acoustic transducer; and
an NPN transistor that is electrically coupled to the current source at its collector and the acoustic transducer at its base.

30. The IC of claim 17, wherein the drive circuitry further comprises:
an inverting gain element that is electrically coupled between a first node and a second node;
a first resistor that is electrically coupled between the first node and the second node;
the acoustic transducer is electrically coupled between the first node and the second node;
a first capacitor that is coupled to the first node; and
a second capacitor that is coupled to the second node.

31. The IC of claim 30, wherein the first and second capacitors further comprise first and second variable capacitors.

32. The IC of claim 17, wherein the acoustic resonance chamber further comprises a tuning member that is adapted to adjust the resonant frequency of the acoustic resonant chamber.

33. The IC of claim 17, wherein the acoustic transducer further comprises a microelectromechanical systems (MEMS) microphone.

34. The IC of claim 33, wherein transfer system further comprises:
an input port that is in fluid communication with the acoustic resonance chamber;
a first MEMS valve that is located between the input port and the acoustic resonance chamber;
a output port that is in fluid communication with the acoustic resonance chamber;
a second MEMS valve that is located between the output port and the acoustic resonance chamber; and
a MEMS pump that is in fluid communication with the output port.

35. The IC of claim 34, wherein the acoustic resonance chamber further comprises a tuning member that is adapted to adjust the resonant frequency of the acoustic resonant chamber.

* * * * *